(12) United States Patent
Chen

(10) Patent No.: US 8,992,563 B2
(45) Date of Patent: Mar. 31, 2015

(54) DELIVERY WIRE ASSEMBLY FOR OCCLUSIVE DEVICE DELIVERY SYSTEM

(75) Inventor: Hancun Chen, San Ramon, CA (US)

(73) Assignee: Boston Scientific Scimed, Inc., Maple Grove, MN (US)

(*) Notice: Subject to any disclaimer, the term of this patent is extended or adjusted under 35 U.S.C. 154(b) by 110 days.

(21) Appl. No.: 12/913,177

(22) Filed: Oct. 27, 2010

(65) Prior Publication Data

US 2011/0106128 A1     May 5, 2011

Related U.S. Application Data

(60) Provisional application No. 61/257,156, filed on Nov. 2, 2009.

(51) Int. Cl.
*A61B 17/00* (2006.01)
*A61B 17/12* (2006.01)

(52) U.S. Cl.
CPC ..... *A61B 17/12022* (2013.01); *A61B 17/12109* (2013.01); *A61B 17/12145* (2013.01); *A61B 17/1215* (2013.01); *A61B 17/12154* (2013.01); *A61B 2017/12063* (2013.01)
USPC ....................................................... 606/200

(58) Field of Classification Search
CPC .................... A61B 17/1214; A61B 17/12145; A61B 17/1215; A61B 17/12154
USPC .................. 606/108, 200, 194, 198; 600/585; 604/57, 103.09, 524
See application file for complete search history.

(56) References Cited

U.S. PATENT DOCUMENTS

| | | | |
|---|---|---|---|
| 4,994,069 A | 2/1991 | Ritchart et al. | |
| 5,423,829 A * | 6/1995 | Pham et al. | 606/108 |
| 5,830,155 A * | 11/1998 | Frechette et al. | 600/585 |
| 6,684,884 B2 | 2/2004 | Nikolchev et al. | |

(Continued)

FOREIGN PATENT DOCUMENTS

| | | |
|---|---|---|
| EP | 0739607 A2 | 10/1996 |
| WO | 95/07732 | 3/1995 |
| WO | 2008/144587 A2 | 11/2008 |

OTHER PUBLICATIONS

PCT International Search Report and Written Opinion for PCT/US2010/054228, Applicant Boston Scientific Scimed, Inc., Forms PCT/ISA/220, 210, and 237 dated Dec. 27, 2010 (14 pages).

(Continued)

*Primary Examiner* — Darwin Erezo
*Assistant Examiner* — Martin T Ton
(74) *Attorney, Agent, or Firm* — Kacvinsky Daisak Bluni PLLC

(57) ABSTRACT

A delivery wire assembly for delivering an occlusive device to a location in a patient's vasculature, includes delivery wire conduit defining a conduit lumen, a core wire disposed in the conduit lumen, the core wire having a distal detachment zone, and an enhancing coil disposed around the distal detachment zone, the enhancing coil configured to transfer a distally directed force from the delivery wire assembly to objects located distal of the delivery wire assembly without damaging the distal detachment zone. In one embodiment, the enhancing coil includes a proximal section having a first diameter, a distal section having a diameter larger than the diameter of the proximal section, and a transition section connecting the respective proximal and distal sections, wherein the transition section flares radially in a distal direction.

12 Claims, 5 Drawing Sheets

(56) References Cited

U.S. PATENT DOCUMENTS

| | | |
|---|---|---|
| 2002/0038132 A1 | 3/2002 | Abrams |
| 2004/0034378 A1 | 2/2004 | Monstadt et al. |
| 2006/0135986 A1 | 6/2006 | Wallace et al. |
| 2006/0282112 A1 | 12/2006 | Griffin |
| 2007/0123927 A1* | 5/2007 | Farnan .......................... 606/200 |
| 2009/0062726 A1* | 3/2009 | Ford et al. ....................... 604/57 |
| 2009/0076540 A1 | 3/2009 | Marks et al. |
| 2009/0143786 A1 | 6/2009 | Bashiri et al. |

OTHER PUBLICATIONS

PCT International Search Report and Written Opinion for PCT/US2010/054206, Applicant Boston Scientific Scimed, Inc., Forms PCT/ISA/210, 220, and 237, dated Oct. 27, 2010 (10 pages).

* cited by examiner

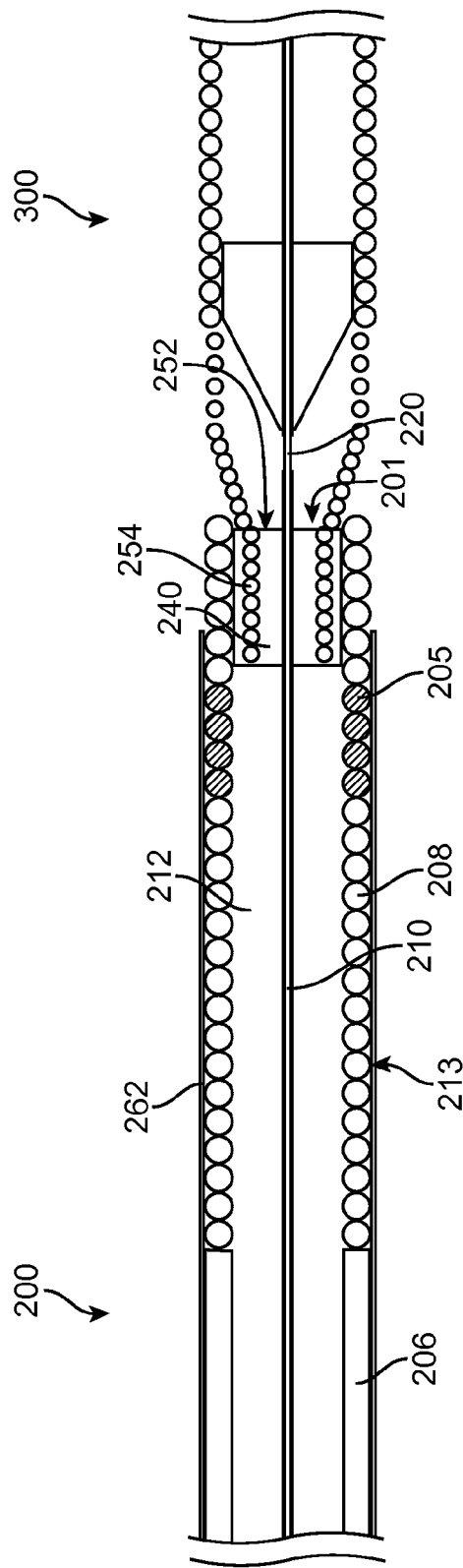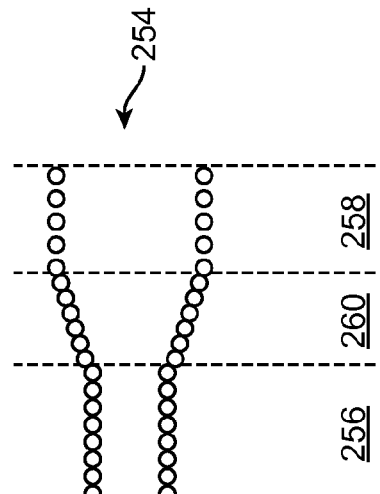
FIG. 4
FIG. 5

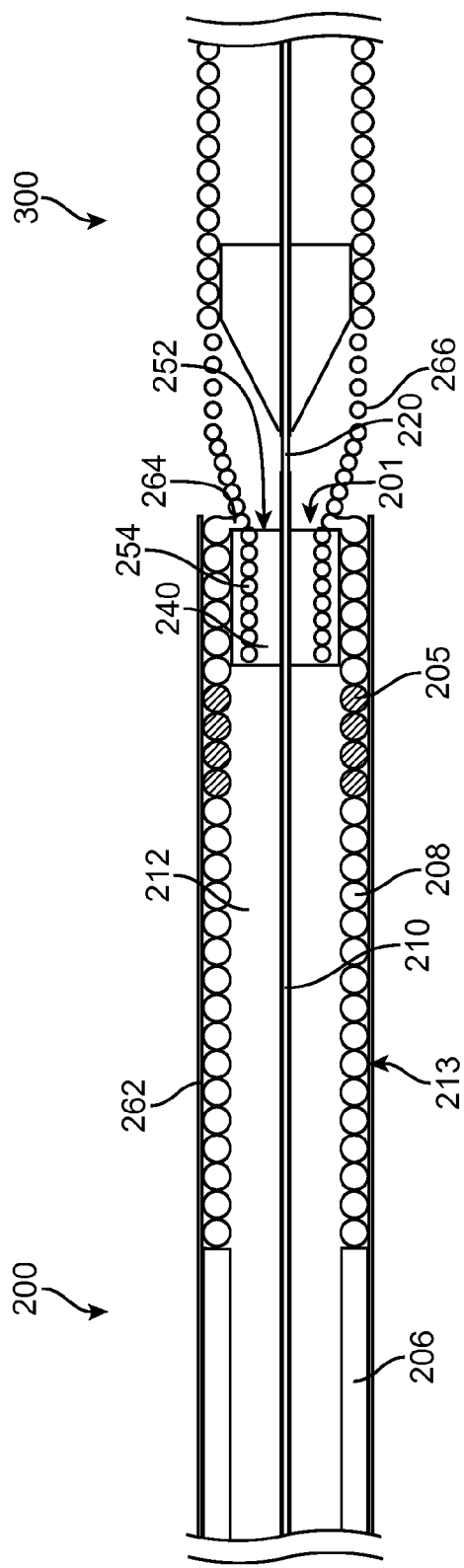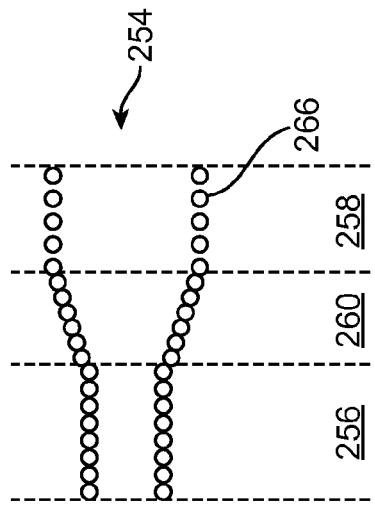
FIG. 6
FIG. 7

US 8,992,563 B2

DELIVERY WIRE ASSEMBLY FOR OCCLUSIVE DEVICE DELIVERY SYSTEM

RELATED APPLICATION DATA

The present application claims the benefit under 35 U.S.C. §119 to U.S. provisional patent application Ser. No. 61/257,156, filed Nov. 2, 2009. The foregoing application is hereby incorporated by reference into the present application in its entirety.

FIELD

The field of the disclosed inventions generally relates to systems and delivery devices for implanting vaso-occlusive devices for establishing an embolus or vascular occlusion in a vessel of a human or veterinary patient. More particularly, the invention relates to a delivery wire assembly.

BACKGROUND

Vaso-occlusive devices or implants are used for a wide variety of reasons, including treatment of intra-vascular aneurysms. Commonly used vaso-occlusive devices include soft, helically wound coils formed by winding a platinum (or platinum alloy) wire strand about a "primary" mandrel. The coil is then wrapped around a larger, "secondary" mandrel, and heat treated to impart a secondary shape. For example, U.S. Pat. No. 4,994,069, issued to Ritchart et al., describes a vaso-occlusive coil that assumes a linear, helical primary shape when stretched for placement through the lumen of a delivery catheter, and a folded, convoluted secondary shape when released from the delivery catheter and deposited in the vasculature.

In order to deliver the vaso-occlusive devices to a desired site in the vasculature, e.g., within an aneurismal sac, it is well-known to first position a small profile, delivery catheter or "micro-catheter" at the site using a steerable guidewire. Typically, the distal end of the micro-catheter is provided, either by the attending physician or by the manufacturer, with a selected pre-shaped bend, e.g., 45°, 90°, "J", "S", or other bending shape, depending on the particular anatomy of the patient, so that it will stay in a desired position for releasing one or more vaso-occlusive device(s) into the aneurysm once the guidewire is withdrawn. A delivery or "pusher" wire is then passed through the micro-catheter, until a vaso-occlusive device coupled to a distal end of the delivery wire is extended out of the distal end opening of the micro-catheter and into the aneurysm. The vaso-occlusive device is then released or "detached" from the end delivery wire, and the delivery wire is withdrawn back through the catheter. Depending on the particular needs of the patient, one or more additional occlusive devices may be pushed through the catheter and released at the same site.

One well-known way to release a vaso-occlusive device from the end of the pusher wire is through the use of an electrolytically severable junction, which is a small exposed section or detachment zone located along a distal end portion of the pusher wire. The detachment zone is typically made of stainless steel and is located just proximal of the vaso-occlusive device. An electrolytically severable junction is susceptible to electrolysis and disintegrates when the pusher wire is electrically charged in the presence of an ionic solution, such as blood or other bodily fluids. Thus, once the detachment zone exits out of the catheter distal end and is exposed in the vessel blood pool of the patient, a current applied through an electrical contact to the conductive pusher wire completes an electrolytic detachment circuit with a return electrode, and the detachment zone disintegrates due to electrolysis.

In "monopolar" systems, return electrodes include electrodes attached to the patient's skin and conductive needles inserted through the skin at a remote site. In "bipolar" systems, return electrodes are located on the pusher wire, e.g. on a delivery wire conduit, but electrically insulated from the conductive path ending in the detachment zone. The anode is made up of a polyimide insulated core wire, which runs through the pusher wire, is attached to the electrical contact at the proximal end, and forms the detachment zone at the distal end.

Perceived problems with current vaso-occlusive coil delivery systems include buckling, kinking, or bending of the exposed detachment zone of the pusher wire. The detachment zone is typically the weakest part of the pusher wire structure. Buckling, kinking, or bending may lead to fatigue failure and premature detachment as the vaso-occlusive coil and pusher wire are navigated through a patient's vascular system. For instance, the detachment zone may fail as the pusher wire is withdrawn to position the attached vaso-occlusive coil, separating the vaso-occlusive coil from the pusher wire. Such premature detachment would require another procedure to retrieve the misplaced vaso-occlusive coil.

SUMMARY

In accordance with embodiments of the disclosed inventions, a delivery wire assembly is provided for delivering an occlusive device to a location in a patient's vasculature, includes delivery wire conduit defining a conduit lumen, a core wire disposed in the conduit lumen, the core wire having a distal detachment zone, and an enhancing coil disposed around the distal detachment zone, the enhancing coil preferably configured to transfer a distally directed force from the delivery wire assembly to objects located distal of the delivery wire assembly without damaging the distal detachment zone. In some embodiments, the enhancing coil includes a proximal section having a first diameter, a distal section having a diameter larger than the diameter of the proximal section, and a transition section connecting the respective proximal and distal sections, wherein the transition section flares radially in a distal direction.

In some embodiments, at least a portion of the proximal section of the enhancing coil is disposed in the conduit lumen. In other embodiments, the proximal section of the enhancing coil is disposed entirely outside of the conduit lumen. In some embodiments, the enhancing coil is secured to the respective delivery wire conduit and the core wire by a conductive adhesive. By way of non-limiting example, the enhancing coil may be electrically connected to the delivery wire conduit, so as to form a portion of a cathode of an electrolytic detachment circuit. In some embodiments, the distal section of the enhancing coil has an open pitch.

It will be appreciated that the delivery wire assembly may be provided as a part of a system for delivering an occlusive device to a location in a patient's vasculature, the system additionally including a delivery catheter defining a catheter lumen, wherein the delivery wire assembly is configured to be slidably inserted into and through the lumen of the delivery catheter. The system further includes an occlusive device detachably connected to the distal detachment zone, and a power supply electrically connected to the delivery wire assembly, wherein the enhancing coil is not directly attached to the occlusive device. In such systems, the enhancing coil is preferably configured to transfer a distally directed force from the delivery wire assembly to push the occlusive device through a patient's vasculature without damaging the distal detachment zone.

In one embodiment, a delivery wire assembly is provided for delivering an occlusive device to a location in a patient's vasculature, the delivery wire assembly including a delivery wire conduit defining a conduit lumen, a core wire disposed in the conduit lumen, the core wire having a distal detachment zone, and an enhancing coil disposed around the distal detachment zone, the enhancing coil comprising a proximal section having a first diameter, a distal section having a diameter larger than the diameter of the proximal section, and a transition section connecting the respective proximal and distal sections, wherein the enhancing coil is electrically connected to the delivery wire conduit and forms a portion of a cathode of an electrolytic detachment circuit, wherein the distal section of the enhancing coil has an open pitch, and wherein the enhancing coil is configured to transfer a distally directed force from the delivery wire assembly to objects located distal of the delivery wire assembly without damaging the distal detachment zone.

In such embodiment, the transition section of the enhancing coil may flares radially in a distal direction. At least a portion of the proximal section of the enhancing coil may be disposed in the conduit lumen. Alternatively, the proximal section of the enhancing coil may be disposed entirely outside of the conduit lumen. In some embodiments, the enhancing coil is secured to both the delivery wire conduit and the core wire by an adhesive.

Other and further aspects and features of embodiments of the disclosed inventions will become apparent from the ensuing detailed description in view of the accompanying figures.

BRIEF DESCRIPTION OF THE DRAWINGS

Referring now to the drawings in which like reference numbers represent corresponding parts throughout, and in which:

FIG. 4 is a longitudinal cross-sectional view of a delivery wire assembly connected to an occlusive coil, according to one embodiment.

FIG. 5 is a longitudinal cross-sectional view of an enhancing coil, according to the embodiment in FIG. 4.

FIG. 6 is a longitudinal cross-sectional view of a delivery wire assembly connected to an occlusive coil, according to another embodiment.

FIG. 7 is a longitudinal cross-sectional view of an enhancing coil, according to the embodiment in FIG. 6.

DETAILED DESCRIPTION OF THE ILLUSTRATED EMBODIMENTS

Figure 1:
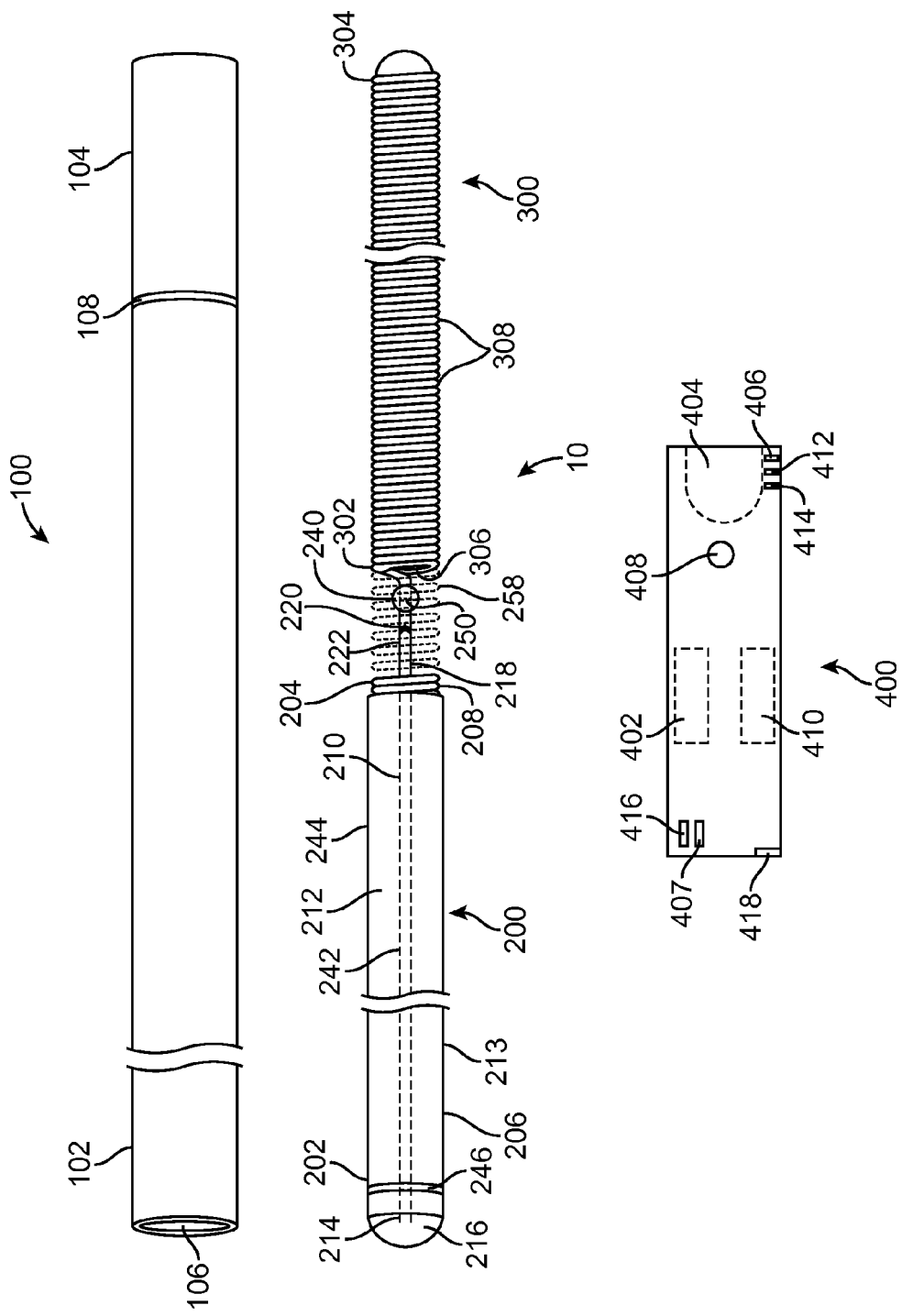
FIG. 1 illustrates an occlusive coil delivery system, according to one embodiment, with parts of the core wire and enhancing coil shown in shadow for clarity.

FIG. 1 illustrates an occlusive coil delivery system 10 according to one embodiment of the disclosed inventions. The system 10 includes a number of subcomponents or subsystems. These include a delivery catheter 100, a delivery wire assembly 200, an occlusive coil 300, and a power supply 400. The delivery catheter 100 includes a proximal end 102, a distal end 104, and a lumen 106 extending between the proximal and distal ends 102, 104. The lumen 106 of the delivery catheter 100 is sized to accommodate axial movement of the delivery wire assembly 200. Further, the lumen 106 is sized for the passage of a guidewire (not shown) which may optionally be used to properly guide the delivery catheter 100 to the appropriate delivery site.

The delivery catheter 100 may include a braided-shaft construction of stainless steel flat wire that is encapsulated or surrounded by a polymer coating. By way of non-limiting example, HYDROLENE® is a polymer coating that may be used to cover the exterior portion of the delivery catheter 100. Of course, the system 10 is not limited to a particular construction or type of delivery catheter 100 and other constructions known to those skilled in the art may be used for the delivery catheter 100.

The inner lumen 106 may be advantageously coated with a lubricious coating such as PTFE to reduce frictional forces between the delivery catheter 100 and the respective delivery wire assembly 200 and occlusive coil 300 being moved axially within the lumen 106. The delivery catheter 100 may include one or more optional marker bands 108 formed from a radiopaque material that can be used to identify the location of the delivery catheter 100 within the patient's vasculature system using imaging technology (e.g., fluoroscope imaging). The length of the delivery catheter 100 may vary depending on the particular application, but generally is around 150 cm in length. Of course, other lengths of the delivery catheter 100 may be used with the system 10 described herein.

The delivery catheter 100 may include a distal end 104 that is straight as illustrated in FIG. 1. Alternatively, the distal end 104 may be pre-shaped into a specific geometry or orientation. For example, the distal end 104 may be shaped into a "C" shape, an "S" shape, a "J" shape, a 45° bend, a 90° bend. The size of the lumen 106 may vary depending on the size of the respective delivery wire assembly 200 and occlusive coil 300, but generally the diameter of the lumen 106 of the delivery catheter 100 (I.D. of delivery catheter 100) is less than about 0.02 inches. The delivery catheter 100 is known to those skilled in the art as a microcatheter. While not illustrated in FIG. 1, the delivery catheter 100 may be utilized with a separate guide catheter (not shown) that aids in guiding the delivery catheter 100 to the appropriate location within the patient's vasculature.

Still referring to FIG. 1, the system 10 includes a delivery wire assembly 200 configured for axial movement within the lumen 106 of the delivery catheter 100. The delivery wire assembly 200 generally includes a proximal end 202 and a distal end 204. The delivery wire assembly 200 includes a delivery wire conduit 213, which has a proximal tubular portion 206 and a distal coil portion 208. The proximal tubular portion 206 may be formed from, for example, a flexible stainless steel hypotube. The distal coil portion 208 may be formed from, for example, stainless steel wire. The distal coil portion 208 may be joined to the proximal tubular portion 206 in an end-to-end arrangement.

The delivery wire assembly 200 further includes a core wire 210 that extends from the proximal end 202 of the delivery wire assembly 200 to a location that is distal with respect to the distal end 204 of the delivery wire assembly 200. The core wire 210 is disposed within a conduit lumen 212 that extends within an interior portion of the delivery wire conduit 213. The distal end of the conduit lumen 212 is sealed with a stopper 252. The stopper 252 is made of an enhancing coil 254 and an adhesive 240 that secures the enhancing coil 254 to the delivery wire conduit 213 and the core wire 210.

The enhancing coil 254 shown in FIGS. 4 and 5 is wound from a polyimide insulated stainless steel wire. The wire is wound around several mandrels to form the enhancing coil 254. The proximal end of the wire is wound around a smaller mandrel to form a proximal section 256 with smaller coils. The distal end of the wire is wound around a larger mandrel to form a distal section 258 with larger coils. The middle of the wire is wound around a conical mandrel to form a transition section 260 with smaller coils at the proximal end and larger coils at the distal end.

The smaller proximal section 256 of the enhancing coil 254 is disposed in the distal end of the conduit lumen 212, and serves a centering function. The proximal section 256 of the enhancing coil 254 is secured to both an inside surface of the delivery wire conduit 213 and the core wire 210 with an adhesive 240. Consequently, the delivery wire conduit 213 and the core wire 210 are attached to each other via the enhancing coil 254. The enhancing coil 254 and the adhesive 240 also form a stopper 252, which may provide a liquid tight seal at the distal end of the conduit lumen 212. The enhancing coil 254 is not directly attached to the occlusive coil 300.

Referring to FIG. 1, the core wire 210 is formed from an electrically conductive material such as stainless steel wire. The proximal end 214 of the core wire 210 (shown in phantom) is electrically coupled to an electrical contact 216 located at the proximal end 202 of the delivery wire assembly 200. The electrical contact 216 may be formed from a metallic solder (e.g., gold) that is configured to interface with a corresponding electrical contact (not shown) in the power supply 400. The core wire 210 is connected to the delivery wire conduit 213 as described below.

A portion of the core wire 210 is advantageously coated with an insulative coating 218. The insulative coating 218 may include polyimide. The entire length of the core wire 210 is coated with an insulative coating 218, except for the proximal end 214 of the core wire 210 that contacts the electrical contact 216, and a small region 220 located in a portion of the core wire 210 that extends distally with respect to the distal end 204 of the delivery wire assembly 200. This latter, "bare" portion of the core wire 210 forms the electrolytic detachment zone 220, which dissolves upon application of electrical current from the power supply 400.

As shown in FIG. 4, the core wire 210 functions as a tether to the occlusive coil 300, such that when the delivery wire assembly 200 is pulled proximally, the occlusive coil 300 can also be withdrawn prior to coil detachment. When the occlusive coil 300 and the delivery wire assembly 200 are pushed distally into the delivery catheter 100, the enhancing coil 254 carries the load between the two parts. Because the enhancing coil 254 is joined to the core wire 210 proximal of the detachment zone 220 as shown in FIG. 4, the enhancing coil 254 transfers sufficient distally directed force to the occlusive coil 300 to advance it through a patient's vasculature while protecting the detachment zone 220 from damage.

The larger distal section 258 of the enhancing coil 254 is disposed around the detachment zone 220. It has an open pitch, as shown in FIG. 5, to minimize interference with liquid access to the detachment zone 220. The proximal and transition sections 256, 260 of the enhancing coil 254 can have either open or closed pitch.

Figure 2:
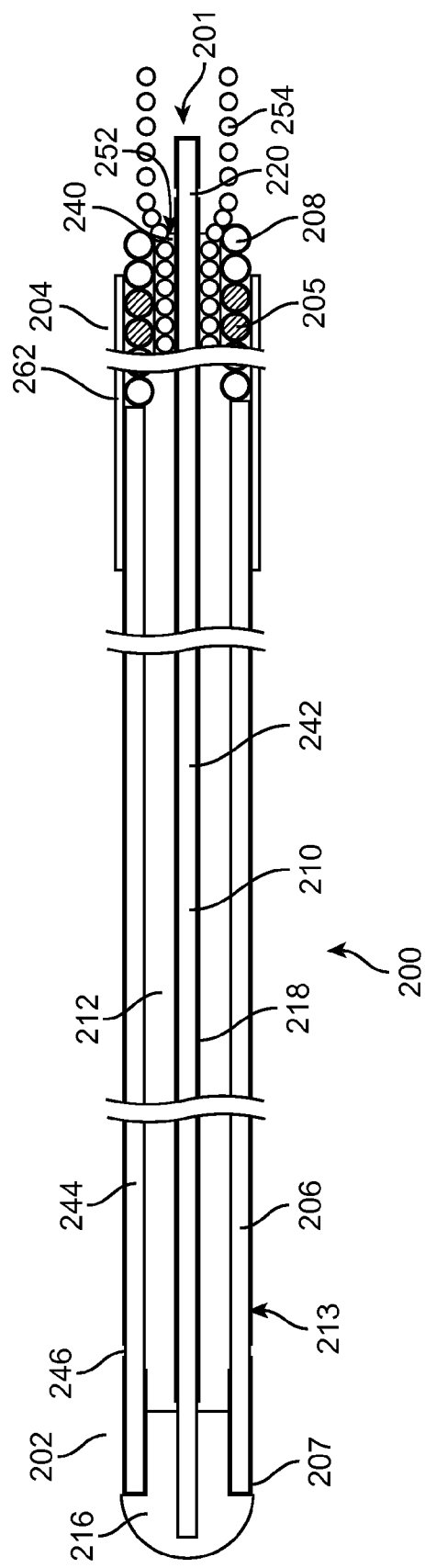
FIG. 2 is a longitudinal cross-sectional view of a delivery wire assembly, according to one embodiment.

FIG. 2 illustrates a longitudinal cross-sectional view of the delivery wire assembly 200 according to one embodiment. Similar elements of this embodiment are identified with the same reference numbers as discussed above with respect to FIG. 1. The delivery wire assembly 200 includes a proximal end 202 and a distal end 204 and measures between around 184 cm to around 186 cm in length. The delivery wire assembly 200 includes a delivery wire conduit 213 with a proximal tubular portion 206, a distal coil portion 208, and a distal opening 201. The proximal tubular portion 206 may be formed from stainless steel hypotube having an outer diameter (OD) of 0.01325 inches and inner diameter (ID) of 0.0075 inches. The length of the hypotube section may be between around 140 cm to around 150 cm.

As seen in FIG. 2, a distal coil portion 208 is joined in end-to-end fashion to the distal face of the proximal tubular portion 206. The joining may be accomplished using a weld or other bond. The distal coil portion 208 may have a length of around 39 cm to around 41 cm in length. The distal coil portion 208 may comprise a coil of 0.0025 inches×0.006 inches. The first dimension generally refers to the OD of the coil wire that forms the coil. The latter dimension generally refers to the internal mandrel used to wind the coil wire around to form the plurality of coil winds and is the nominal ID of the coil. One or more marker coils 205 of the distal coil portion 208 may be formed from a radiopaque material. For example, the distal coil portion 208 may include a segment of stainless steel coil (e.g., 3 cm in length), followed by a segment of platinum coil (which is radiopaque and also 3 mm in length), followed by a segment of stainless steel coil (e.g., 37 cm in length), and so on and so forth.

An outer sleeve 262 or jacket surrounds a portion of the proximal tubular portion 206 and a portion of the distal coil portion 208 of the delivery wire conduit 213. The outer sleeve 262 covers the interface or joint formed between the proximal tubular portion 206 and the distal coil portion 208. The outer sleeve 262 may have a length of around 50 cm to around 54 cm. The outer sleeve 262 may be formed from a polyether block amide plastic material (e.g., PEBAX 7233 lamination). The outer sleeve 262 may include a lamination of PEBAX and HYDROLENE® that may be heat laminated to the delivery wire assembly 200. The OD of the outer sleeve 262 may be less than 0.02 inches and advantageously less than 0.015 inches. During manufacturing, the outer sleeve 262 is removed from the very distal end of the delivery wire conduit 213 to form an exposed return cathode.

The core wire 210, which runs through the delivery wire conduit 213, terminates at electrical contact 216 at one end and extends distally with respect to the distal coil portion 208 of the delivery wire conduit 213 to the core wire distal end 222 at the other end. The core wire 210 is coated with an insulative coating 218 such as polyimide except at the electrolytic detachment zone 220 and the proximal segment coupled to the electrical contact 216. The electrolytic detachment zone 220 is located less and half a millimeter (e.g., about 0.02 mm to about 0.2 mm) distally with respect to the distal end of the distal coil portion 208. The core wire 210 may have an OD of around 0.00175 inches.

Figure 3:
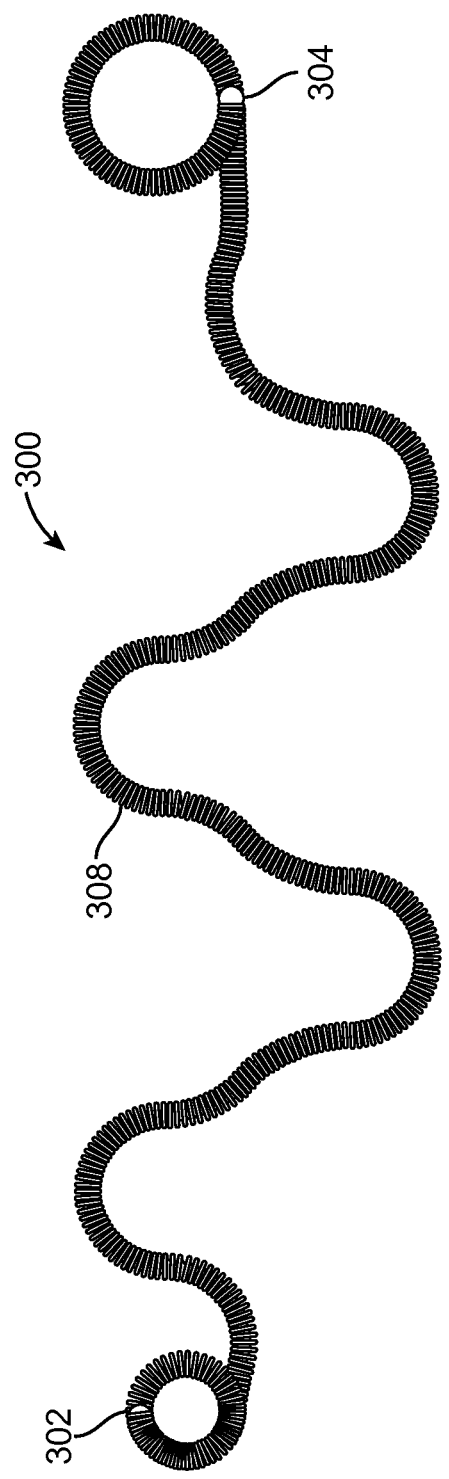
FIG. 3 illustrates an occlusive coil in a natural state mode, illustrating one exemplary secondary configuration.

FIG. 3 illustrates one exemplary configuration of an occlusive coil 300 in a natural state. In the natural state, the occlusive coil 300 transforms from the straight configuration illustrated in, for instance, FIG. 1 into a secondary shape. The secondary shaped may include both two and three dimensional shapes of a wide variety. FIG. 3 is just one example of a secondary shape of an occlusive coil 300 and other shapes and configurations are contemplated to fall within the scope of the disclosed inventions. Also, the occlusive coil 300 may incorporate synthetic fibers over all or a portion of the occlusive coil 300 as is known in the art. These fibers may be attached directly to coil windings 308 or the fibers may be integrated into the occlusive coil 300 using a weave or braided configuration.

The occlusive coil 300 includes a proximal end 302, a distal end 304, and a lumen 306 extending there between. The occlusive coil 300 is generally made from a biocompatible metal such as platinum or a platinum alloy (e.g., platinumtungsten alloy). The occlusive coil 300 generally includes a straight configuration (as illustrated in FIG. 1) when the occlusive coil 300 is loaded within the delivery catheter 100. Upon release, the occlusive coil 300 generally takes a secondary shape which may include three-dimensional helical configurations such as those illustrated in FIG. 3.

The occlusive coil 300 includes a plurality of coil windings 308. The coil windings 308 are generally helical about a central axis disposed along the lumen 306 of the occlusive coil 300. The occlusive coil 300 may have a closed pitch configuration as illustrated in FIG. 1. Of course, the system 10 described herein may be used with occlusive coils 300 or other occlusive structures having a variety of configurations, and is not limited to occlusive coils 300 having a certain size or configuration. Additional features or components might be used to provide mechanical interlock between the delivery wire 200 and occlusive coil 300.

The distal end 222 of the core wire 210, which includes the electrolytic detachment zone 220, is connected to the proximal end 302 of the occlusive coil 300 at a junction 250. Various techniques and devices can be used to connect the core wire 210 to the occlusive coil 300, including laser melting, and laser tack, spot, and continuous welding. It is preferable to apply an adhesive 240 to cover the junction 250 formed between the distal end 222 of the core wire 210 and the proximal end 302 of the occlusion coil 300. The adhesive 240 may include an epoxy material which is cured or hardened through the application of heat or UV radiation. For example, the adhesive 240 may include a thermally cured, two-part epoxy such as EPO-TEK® 353ND-4 available from Epoxy Technology, Inc., 14 Fortune Drive, Billerica, Mass. The adhesive 240 encapsulates the junction 250 and increases its mechanical stability.

As shown in FIG. 1, the system 10 further includes a power supply 400 for supplying direct current to the core wire 210, which contains the electrolytic detachment zone 220. In the presence of an electrically conductive fluid (including a physiological fluid such as blood, or an electrically conductive flushing solution such as saline), activation of the power supply 400 causes electrical current to flow in a circuit including the core wire electrical contact 216, the core wire 210, the electrolytic detachment zone 220, and a return electrode (not shown). After several seconds (generally less than about 10 seconds), the sacrificial electrolytic detachment zone 220 dissolves, and the occlusive coil 300 separates form the core wire 210.

The power supply 400 preferably includes an onboard energy source, such as batteries (e.g., a pair of AAA batteries), along with drive circuitry 402. The drive circuitry 402 may include one or more microcontrollers or processors configured to output a driving current. The power supply 400 illustrated in FIG. 1 includes a receptacle 404 configured to receive and mate with the proximal end 202 of the delivery wire assembly 200. Upon insertion of the proximal end 202 into the receptacle 404, the electrical contact 216 disposed on the delivery wire assembly 200 electrically couple with corresponding contacts (not shown) located in the power supply 400.

A visual indicator 406 (e.g., LED light) is used to indicate when the proximal end 202 of delivery wire assembly 200 has been properly inserted into the power supply 400. Another visual indicator 407 is activated if the onboard energy source needs to be recharged or replaced. The power supply 400 includes an activation trigger or button 408 that is depressed by the user to apply the electrical current to the sacrificial electrolytic detachment zone 220. Once the activation trigger 408 has been activated, the driver circuitry 402 automatically supplies current until detachment occurs. The drive circuitry 402 typically operates by applying a substantially constant current, e.g., around 1.5 mA.

The power supply 400 may include optional detection circuitry 410 that is configured to detect when the occlusive coil 300 has detached from the core wire 210. The detection circuitry 410 may identify detachment based upon a measured impedance value. A visual indicator 412 may indicate when the power supply 400 is supplying adequate current to the sacrificial electrolytic detachment zone 220. Another visual indicator 414 may indicate when the occlusive coil 300 has detached from the core wire 210. As an alternative to the visual indicator 414, an audible signal (e.g., beep) or even tactile signal (e.g., vibration or buzzer) may be triggered upon detachment. The detection circuitry 410 may be configured to disable the drive circuitry 402 upon sensing detachment of the occlusive coil 300.

The power supply 400 may also contain another visual indicator 416 that indicates to the operator when non-bipolar delivery wire assembly is inserted into the power supply 400. As explained in the background above, non-bipolar delivery wire assemblies use a separate return electrode that typically is in the form of a needle that was inserted into the groin area of the patient. The power supply 400 is configured to detect when a non-bipolar delivery wire assembly has been inserted. Under such situations, the visual indicator 416 (e.g., LED) is turned on and the user is advised to insert the separate return electrode (not shown in FIG. 1) into a port 418 located on the power supply 400.

Still referring to FIG. 1, the core wire 210 forms a first conductive path 242 between the electrical contact 216 and the electrolytic detachment zone 220. This first conductive path 242 may comprise the anode (+) of the electrolytic circuit when the delivery wire assembly 200 is operatively coupled to the power supply 400. A second conductive path 244, the return path, is formed by the proximal tubular portion 206 and a distal coil portion 208 of the delivery wire conduit 213. The second conductive path 244 is electrically isolated from the first conductive path 242. The second conductive path 244 may comprise the cathode (−) or ground electrode for the electrical circuit.

A ground contact 246 for the second conductive path 244 may be disposed on a proximal end of the tubular portion 206 of the delivery wire conduit 213. In one embodiment, the ground contact 246 is simply an exposed portion of the tubular portion 206 since the tubular portion 206 is part of the second conductive path 244. For instance, a proximal portion of the tubular portion 206 that is adjacent to the electrical contact 216 may be covered with an insulative coating 207 such as polyimide as illustrated in FIG. 2. An exposed region of the tubular portion 206 that does not have the insulative coating may form the ground contact 246. Alternatively, the ground contact 246 may be a ring type electrode or other contact that is formed on the exterior of the tubular portion 206.

The ground contact 246 is configured to interface with a corresponding electrical contact (not shown) in the power supply 400 when the proximal end 202 of the delivery wire assembly 200 is inserted into the power supply 400. The ground contact 246 of the second conductive path 244 is, of course, electrically isolated with respect to the electrical contact 216 of the first conductive path 242.

In the embodiment in FIGS. 6 and 7, the outer sleeve 262 is not removed from the very distal end of the delivery wire conduit 213 during manufacturing to form an exposed return cathode. Instead, an electrical connection 264 is made between the delivery wire conduit 213 and the enhancing coil 254. Various techniques can be used to make the electrical connection 264, including laser melting, and laser tack, spot, and continuous welding. Also, the polyimide covering is removed from an area 266 in the distal section 258 of the enhancing coil 254, so that the enhancing coil 254 becomes part of the second conductive path 244 (i.e., the cathode of the electrolytic detachment circuit.)

While various embodiments of the disclosed inventions have been shown and described, they are presented for purposes of illustration, and not limitation. Various modifications may be made to the illustrated and described embodiments (e.g., the dimensions of various parts) without departing from the scope of the disclosed inventions, which is to be defined only by the following claims and their equivalents.

What is claimed is:

1. A delivery wire assembly for delivering an occlusive device to a location in a patient's vasculature, comprising:
    a delivery wire conduit defining a conduit lumen;
    a core wire disposed in the conduit lumen, the core wire having a distal detachment zone; and
    an enhancing coil disposed around the distal detachment zone, the enhancing coil comprising
        a proximal section having a first diameter, the proximal section being secured by an adhesive to an inner surface of the conduit lumen and to the core wire, thereby forming a watertight seal,
        a distal section having a diameter larger than the diameter of the proximal section, and
        a transition section connecting the respective proximal and distal sections, wherein the transition section flares radially in a distal direction,
    wherein the enhancing coil is configured to transfer a distally directed force from the delivery wire assembly to objects located distal of the delivery wire assembly without damaging the distal detachment zone.

2. The delivery wire assembly of claim 1, wherein at least a portion of the proximal section of the enhancing coil is disposed in the conduit lumen.

3. The delivery wire assembly of claim 1, wherein the enhancing coil is electrically connected to the delivery wire conduit.

4. The delivery wire assembly of claim 3, wherein the enhancing coil forms a portion of a cathode of an electrolytic detachment circuit.

5. The delivery wire assembly of claim 1, wherein the distal section of the enhancing coil has an open pitch.

6. A system for delivering an occlusive device to a location in a patient's vasculature, comprising:
    a delivery catheter defining a catheter lumen;
    a delivery wire assembly configured to be slidably inserted into and through the lumen of the delivery catheter, the delivery wire assembly comprising
    a delivery wire conduit defining a conduit lumen,
    a core wire disposed in the conduit lumen, the core wire having a distal detachment zone, and
    an enhancing coil disposed around the distal detachment zone, the enhancing coil comprising
        a proximal section having a diameter, the proximal section being secured by an adhesive to an inner surface of the conduit lumen and to the core wire, thereby forming a watertight seal,
        a distal section having a diameter larger than the diameter of the proximal section, and
        a transition section connecting the respective proximal and distal sections, wherein the transition section flares radially in a distal direction;
    an occlusive device detachably connected to the distal detachment zone; and
    a power supply electrically connected to the delivery wire assembly, wherein the enhancing coil is not directly attached to the occlusive device,
    wherein the enhancing coil is configured to transfer a distally directed force from the delivery wire assembly to push the occlusive device through a patient's vasculature without damaging the distal detachment zone.

7. The occlusive device delivery system of claim 6, wherein at least portion of the proximal section of the enhancing coil is disposed in the conduit lumen.

8. The occlusive device delivery system of claim 6, wherein the enhancing coil is electrically connected to the delivery wire conduit, and the enhancing coil forms a portion of a cathode of an electrolytic detachment circuit.

9. The occlusive device delivery system of claim 6, wherein the distal section of the enhancing coil has an open pitch.

10. A delivery wire assembly for delivering an occlusive device to a location in a patient's vasculature, comprising:
    a delivery wire conduit defining a conduit lumen;
    a core wire disposed in the conduit lumen, the core wire having a distal detachment zone; and
    an enhancing coil disposed around the distal detachment zone, the enhancing coil comprising
    a proximal section having a first diameter, the proximal section being secured by an adhesive to an inner surface of the conduit lumen and to the core wire, thereby forming a watertight seal,
    a distal section having a diameter larger than the diameter of the proximal section, and
    a transition section connecting the respective proximal and distal sections, wherein the enhancing coil is electrically connected to the delivery wire conduit and forms a portion of a cathode of an electrolytic detachment circuit, wherein the distal section of the enhancing coil has an open pitch, and wherein the enhancing coil is configured to transfer a distally directed force from the delivery wire assembly to objects located distal of the delivery wire assembly without damaging the distal detachment zone.

11. The delivery wire assembly of claim 10, wherein the transition section flares radially in a distal direction.

12. The delivery wire assembly of claim 10, wherein at least a portion of the proximal section of the enhancing coil is disposed in the conduit lumen.

* * * * *